United States Patent
Yan et al.

(10) Patent No.: US 9,074,221 B2
(45) Date of Patent: Jul. 7, 2015

(54) HOMOZYGOUS AND HETEROZYGOUS IDH1 GENE-DEFECTIVE CELL LINES DERIVED FROM HUMAN COLORECTAL CELLS

(75) Inventors: Hai Yan, Chapel Hill, NC (US); Darell Bigner, Mebane, NC (US); Christopher Gentry Duncan, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/881,417

(22) PCT Filed: Oct. 25, 2011

(86) PCT No.: PCT/US2011/057615
§ 371 (c)(1),
(2), (4) Date: Jul. 25, 2013

(87) PCT Pub. No.: WO2012/061105
PCT Pub. Date: May 10, 2012

(65) Prior Publication Data
US 2014/0147919 A1 May 29, 2014

Related U.S. Application Data

(60) Provisional application No. 61/406,268, filed on Oct. 25, 2010.

(51) Int. Cl.
*C12N 15/85* (2006.01)
*C12N 15/90* (2006.01)
*C12N 5/09* (2010.01)

(52) U.S. Cl.
CPC .............. *C12N 15/85* (2013.01); *C12N 15/902* (2013.01); *C12N 2799/025* (2013.01); *C12N 2800/30* (2013.01); *C12N 5/0693* (2013.01); *C12N 2510/00* (2013.01)

(58) Field of Classification Search
None
See application file for complete search history.

(56) References Cited

U.S. PATENT DOCUMENTS

2014/0147919 A1 * 5/2014 Yan et al. ...................... 435/366

FOREIGN PATENT DOCUMENTS

WO 2010-028099 A1 3/2011

OTHER PUBLICATIONS

Labussiere, et al. (2010) "IDH1 Gene Mutations: A New Paradigm in Glioma Prognosis and Therapy?", Neuro-Oncology, 15(2): 196-99.*
Kato et al., 'A monoclonal antibody IMab-1 specifically recognizes IDH1 R132H, the most common glioma-derived mutation', Biochemical and Biophysical Research Communications, vol. 390, pp. 547-551 (Oct. 7, 2009).
Capper et al., 'Monoclonal antibody specific for IDH1 R132H mutation', Acta Neuopatholgica, vol. 118, pp. 599-601 (Oct. 2, 2009).
Yan et al., 'IDH1 and IDH2 Mutations in Gliomas', The New England Journal of Medicine, vol. 360, pp. 765-773 (Feb. 19, 2009).
Koivunen et al., 'Tranformation by the (R)-enantiomer of 2-hydroxyglutarate linked to EGLN activation', Nature, vol. 483, pp. 484-488 (Mar. 22, 2012).
International Search Report dated May 7, 2012, of PCT/US2011/057615.

* cited by examiner

*Primary Examiner* — Robert M Kelly
(74) *Attorney, Agent, or Firm* — Banner & Witcoff, Ltd.

(57) ABSTRACT

IDH1 gene-defective cell lines (e.g., IDH1R132H heterozygous) have been made from a robust cell line, HCT116. The IDH1 gene-defective cell lines can be used to determine the effect of IDH1R132H on cell biology, tumorigenesis, and cellular metabolic profiles. These cell lines can be used to test potential therapeutic targets and to screen potential therapeutic agents. Kits and xenografts are also contemplated.

9 Claims, 7 Drawing Sheets

HOMOZYGOUS AND HETEROZYGOUS IDH1 GENE-DEFECTIVE CELL LINES DERIVED FROM HUMAN COLORECTAL CELLS

This invention was made using funds from the U.S. National Institutes of Health, grant number R01CA140316. The U.S. government retains certain rights in the invention under the terms of the grant.

BACKGROUND OF THE INVENTION

Mutations in the isocitrate dehydrogenase genes IDH1 and IDH2 occur at an exceptionally high frequency (80%) in gliomas. The mutations also present in 23% of acute myeloid leukemia, and are rarely observed in other types of cancers. The frequency, specificity, and early timing of IDH mutations provide strong evidence for their importance in tumorigenesis, prognosis and therapeutics. However, the functional effects and significance of IDH mutations in human cancer have not been fully defined. Currently, a major limitation of the field is that there are no cell line models which recapitulate IDH mutation-dependent tumor progression.

SUMMARY OF THE DISCLOSURE

One aspect of the invention is isolated and purified human HCT116 colorectal cancer cells which comprise an IDH1 R132H allele and a wild-type IDH1 allele.

Another aspect of the invention is isolated and purified human HCT116 colorectal cancer cells which comprise and express an IDH1 R132H allele, but the cells express no wild-type IDH1 alleles.

Another aspect of the invention is a pair of isogenic human HCT116 colorectal cancer cell lines having a genotype selected from the group consisting of:
  a. IDH1 R132H/IDH1 wild-type;
  b. IDH1 wild type/IDH1 wild type; and
  c. IDH1 R132H/IDH1 wild-type transcriptionally silenced.

These cell lines can be packaged and provided in kits, i.e., divided or undivided containers with one or more components, such as instructions, other reagents, and devices. The cell lines may also be administered to a suitable recipient animal, such as a nude mouse, to form a xenograft, i.e., a tumor from a different species.

These and other aspects of the present disclosure provide the art with cell lines for screening and testing potential anti-tumor agents and treatments.

DETAILED DESCRIPTION

Figure 1:
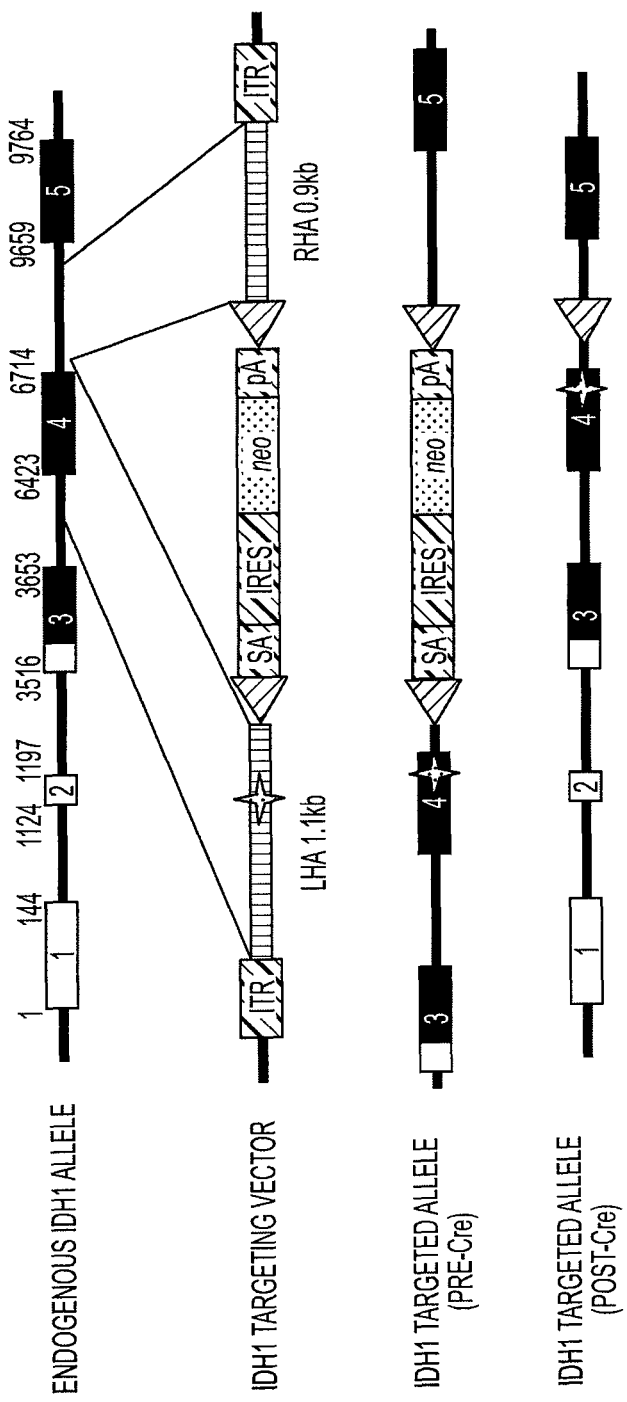
FIG. 1 is a depiction of the strategy used for targeting knock-in of IDH1 R132H alleles in HCT116 cells. The targeting vector was designed to introduce IDH1 R132H mutation in endogenous IDH1 alleles in HCT116 cells. Homology arms (HA) were cloned from HCT116 parent cells and are shown in red. The left HA (LHA) was altered by site-directed mutagenesis to create the IDH1R132H mutation (indicated by yellow star). The homology arms flank a synthetic exon promoter trap (SEPT) cassette. The promoterless SEPT element contains a splice acceptor (SA), internal ribosomal entry sequence (IRES), neomycin selectable marker (neo), and polyadenylation site (pA) which are flanked by LoxP sites (green triangles). Inverted terminal repeats (ITR) of the adeno-associated virus (AAV) vector flank the homology arms. Correctly targeted alleles were infected with Cre adenovirus to excise selectable element generating a clone which differs from the parental cell line by essentially a single base pair.

The inventors have established and characterized stable, long-term human colorectal cells that are homozygous or heterozygous for mutations in the IDH1 gene. The established cell lines provide a means to study the effects conferred by IDH 1 on tumor cells and are useful tools to test different therapeutic approaches in disease models. In some cell lines created, an allele is present but not expressed. In some cell lines both alleles are expressed.

The effect of IDH1 gene mutations in human cancer cells can be studied by using and comparing cell lines having a different IDH1 status (e.g., IDH1R132H heterozygous and IDH1R132H wild-type) from human colorectal cancer cell lines. The impact of IDH1R132H on cellular biology, tumorigenesis, and metabolic profiles can be assessed. Moreover, these cell lines can be used for the identifying therapeutic targets and for screening of novel therapeutic agents.

Any means known in the art to generate a cell line which comprises a defective IDHI gene can be used to obtain the IDH1 gene-defective cells. For example, a colorectal cell line can be used to give rise to an isogenic IDH1 negative cell line by promoterless homologus recombination (see, e.g., Waldman, T. et al. (1995) *Cancer Res.* 55:5187-5190, the contents of which are expressly incorporated by reference). A cell with two wild-type alleles of the IDH1 gene is a gene-normal cell, for purposes of the present disclosure. Preferably, the IDH1 gene-defective cell used in the assay is the same type of cell (i.e., organ source or cell line) as the IDH1 gene-defective cell. More preferably, the two cell lines are isogenic.

The effect of test agents or treatments on the cell lines provided and comparing the effects, provides an indication of the ultimate usefulness of an agent or treatment for therapy of cancers. Particular cancers of interest are gliomas and acute myelogenous leukemia. Any method for a death effect or a cell inhibitory effect can be used. The tests can be done in culture or in whole animals with xenografts. A few particular assays for cell death, cell viability, apoptosis, and killing are described below, but any that are known in the art can be used.

It is well known in the art that viability of a cell can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for this purpose is trypan blue. Viability of cells can also be determined by detecting DNA synthesis. Cells can be cultured in cell medium with labeled nucleotides, e.g., $^3$H-Thymidine. The uptake or incorporation of the labeled nucleotides indicates DNA synthesis. In addition, counting colonies or otherwise assessing cell number can be used as a way to assess cell growth and is another way to test viability of the cells.

Apoptosis is a specific mode of cell death recognized by a characteristic pattern of morphological, biochemical, and molecular changes. Cells going through apoptosis appear shrunken, and rounded; they also can be observed to become detached from culture dish. The morphological changes involve a characteristic pattern of condensation of chromatin and cytoplasm which can be readily identified by microscopy. When stained with a DNA-binding dye, e.g., H33258, apoptotic cells display classic condensed and punctate nuclei instead of homogeneous and round nuclei.

A hallmark of apoptosis is endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome, i.e., 120 base pair. This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the scope of the present disclosure.

Abnormal DNA breaks are also characteristic of apoptosis and can be detected by any means known in the art. In one preferred embodiment, DNA breaks are labeled with biotinylated dUTP (b-dUTP). Cells are fixed and incubated in the presence of biotinylated dUTP with either exogenous terminal transferase (terminal DNA transferase assay; TdT assay) or DNA polymerase (nick translation assay; NT assay). The biotinylated dUTP is incorporated into the chromosome at the places where abnormal DNA breaks are repaired, and are detected with fluorescein conjugated to avidin under fluorescence microscopy.

It may be desirable to screen for potential anti-tumor agents is by incubating a mouse xenograft derived from IDH1 gene-defective cells described here in the presence or absence of a test compound (e.g., an anti-tumor agent), determining tumor morphology (e.g., size, growth, etc.), and selecting a test compound which has the desired effects on the tumor. Desirably the test compound causes the tumor to regress, delay growth, inhibit growth. Similar tests can be performed in vitro. Typically in vitro testing will precede in vivo testing. Xenografts can be removed and maintained or studied in vitro.

Of course, kits for screening various agents, e.g., chemotherapeutic agents, test compounds, anti-tumor agents, and the like and for any other usage as described herein, are easily assembled, and may contain (1) container(s) containing the cell line(s) of the present disclosure; (2) media for propagating cells, and (3) reagents and/or apparatus for detecting morphological, physiological and/or genetic responses to the cell lines, including cell viability. Other components routinely found in such kits may also be included together with instructions for use.

The use of "including," "comprising," "having," "containing," "involving," and variations thereof herein, is meant to encompass the items listed thereafter and equivalents thereof as well as additional items. The articles "a" and "an" are used herein to refer to one or to more than one (i.e. at least one) of the grammatical object of the article. By way of example, "an element" means at least one element and can include more than one element. The term "cell line," as used herein, refers to individual cells, harvested cells, and cultures containing the cells, so long as they are derived from cells of the cell line referred to. A cell line is said to be "continuous," "immortal," or "stable" if the line remains viable over a prolonged time, typically at least about six (6) months. Preferably, the cells remain viable for at least 40 passages. A cell line is said to be "malignant" or "tumorigenic" if, when the cell line is injected into a host, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal.

The following examples are provided for exemplification purposes only and are not intended to limit the scope of the disclosure which has been described in broad terms above.

EXAMPLES

Example 1

Generation of IDH1R132H Isogenic Human Colorectal Cancer Cell Lines

Figure 2:
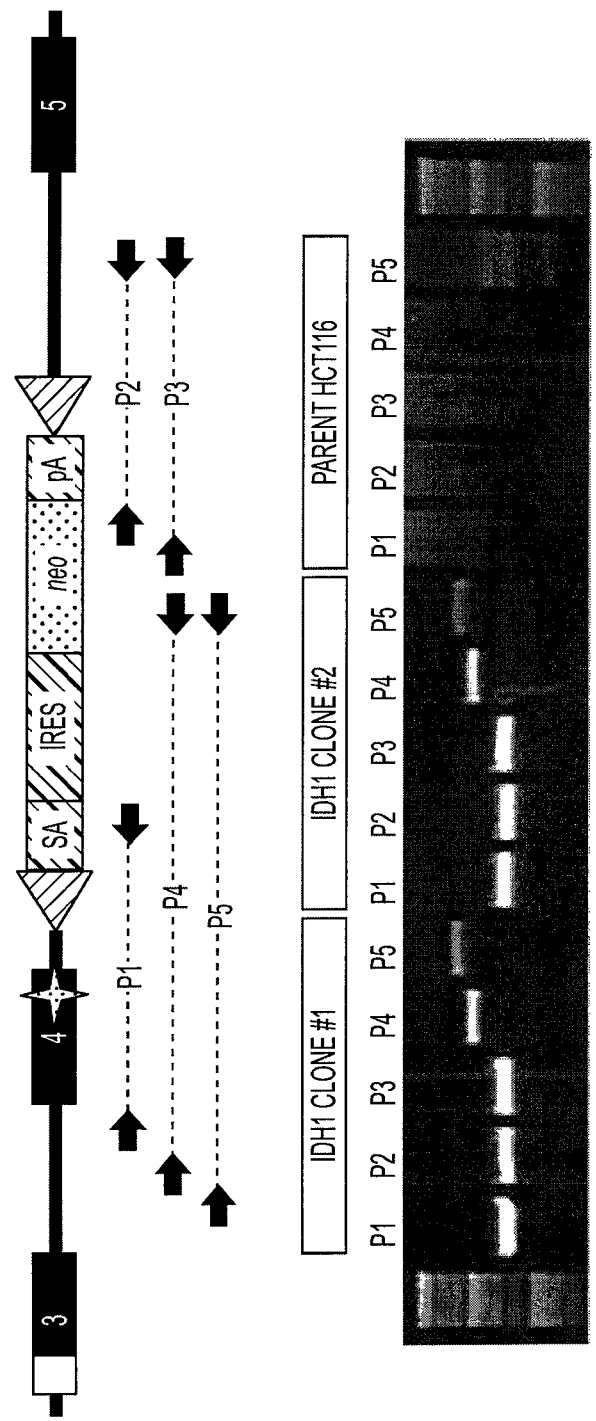
FIG. 2 shows a diagnostic PCR screen for homologous recombination. Diagnostic PCR primer pairs are indicated as P1-P5. The screening approach employs one primer that anneals within the SEPT element and a second primer that is outside the homology region. Five primer sets confirm homologous integration for clones #1 and #2, but not for the parent HCT116 cells. A total of seventeen positive clones were identified.
Figure 3:
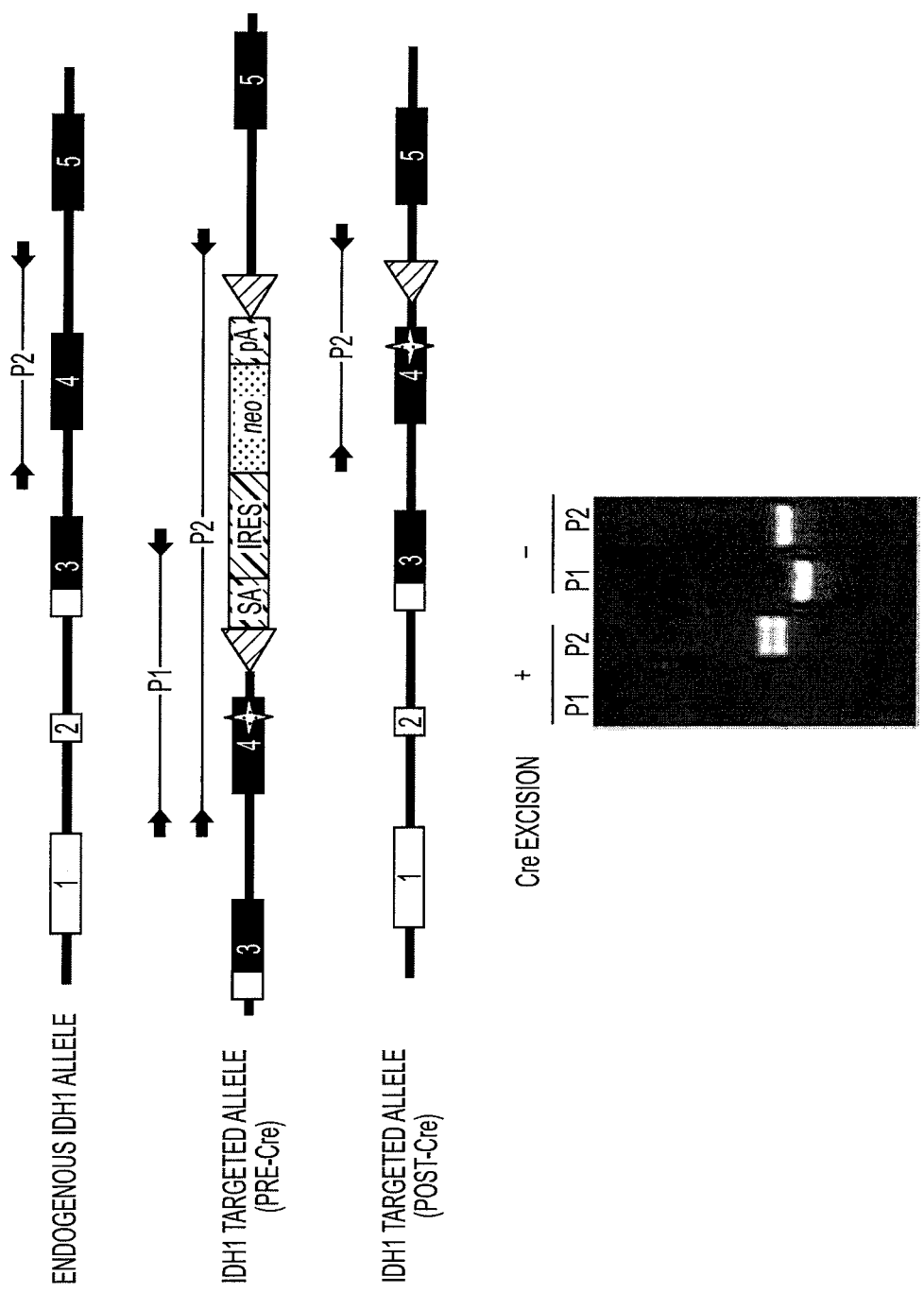
FIG. 3 shows a diagnostic PCR screen for excision of selectable element. Diagnostic PCR primer pairs are indicated as P1 and P2. P1 employs one primer that anneals within the SEPT element and a second primer that is outside the homology region, detecting alleles with intact selectable elements. P2 employs one primer that anneals outside the homology region and a second that anneals beyond the second loxP site, amplifying both WT and targeted alleles, differing by the 34 bp loxP sequence. Recombinant clones were infected with Ad-Cre, diluted to single cell, and analyzed by diagnostic PCR. Representative excised and non-excised clones are depicted. A total of two positive recombinant clones were expanded for experimental procedures. Compete excision was confirmed through analysis of G418 sensitivity.
Figure 4:
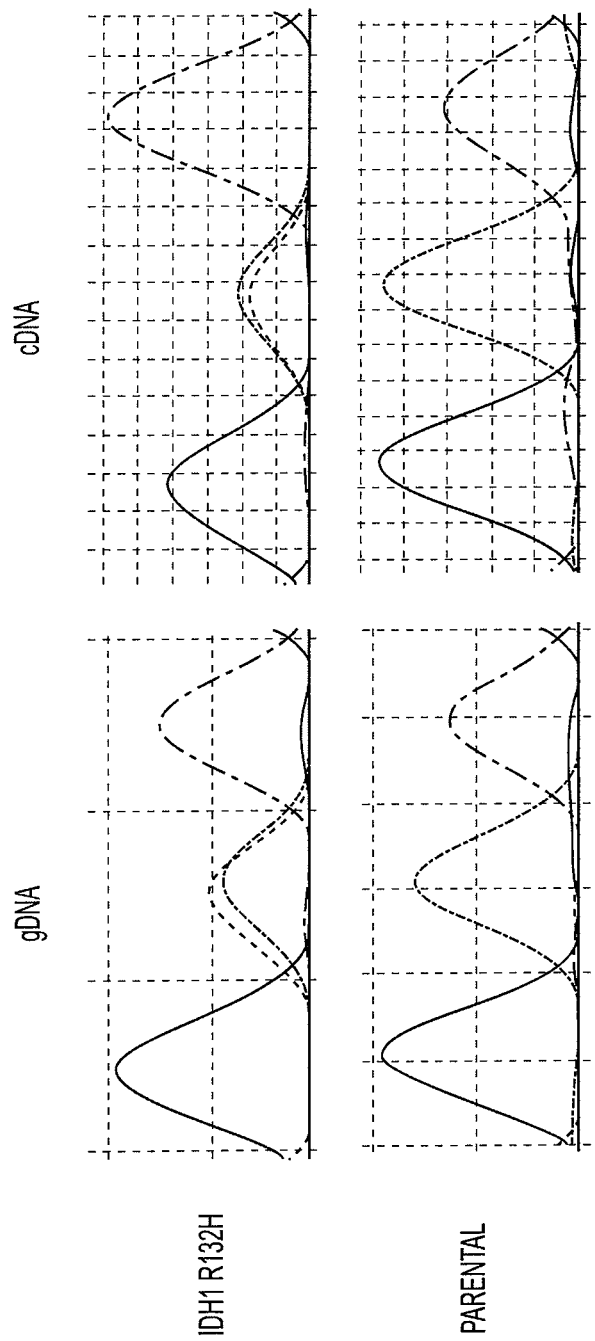
FIG. 4 shows sequencing validation of IDH1-R132H knock-in clones, expressing both wild-type and mutant IDH1. Representative sequencing chromatograms for IDH1 codon 132 in genomic DNA (left) and cDNA (right). Knock-in clones are heterozygous for wild-type allele (CGT) and mutant allele (CAT) coding for an Arginine (R) to Histidine (H) change at position 132.
Figure 5:
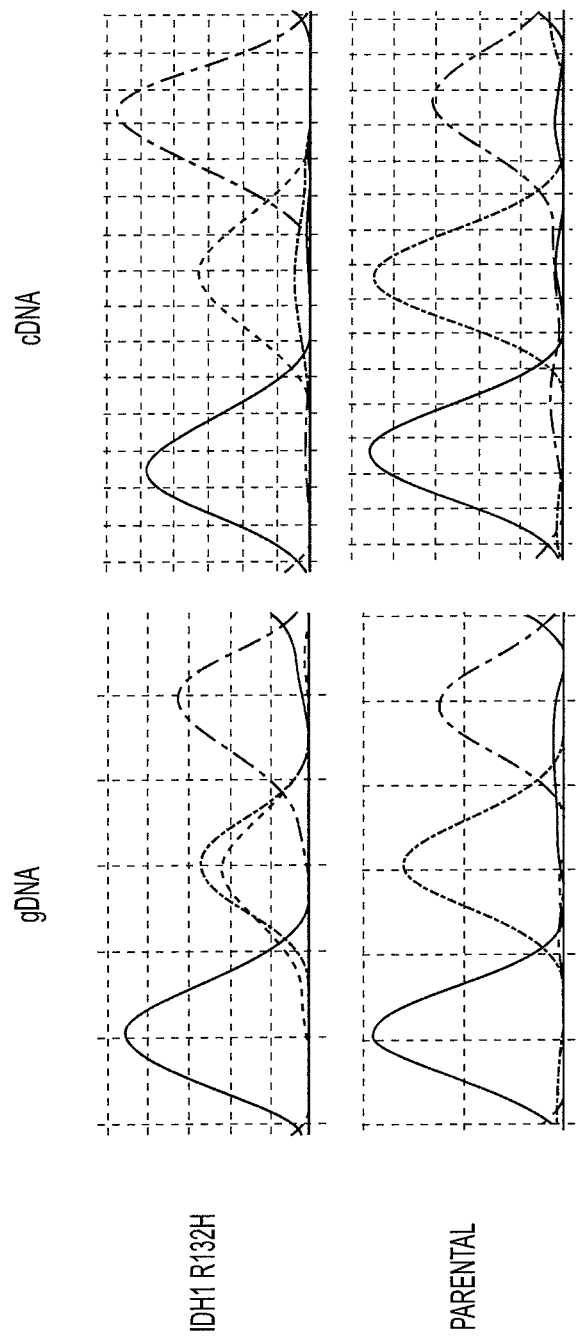
FIG. 5 shows sequencing validation of an IDH1-R132H knock-in clone, expressing only the mutant IDH1R132H. Representative sequencing chromatograms for IDH1 codon 132 in genomic DNA (left) and cDNA (right). Knock-in clone gDNA is heterozygous for wild-type allele (CGT) and mutant allele (CAT) coding for an Arginine (R) to Histidine (H) change at position 132. Wild-type allele is silenced in one knock-in clone cDNA, resulting in predominant mutant allele (CAT) signal.
Figure 6:
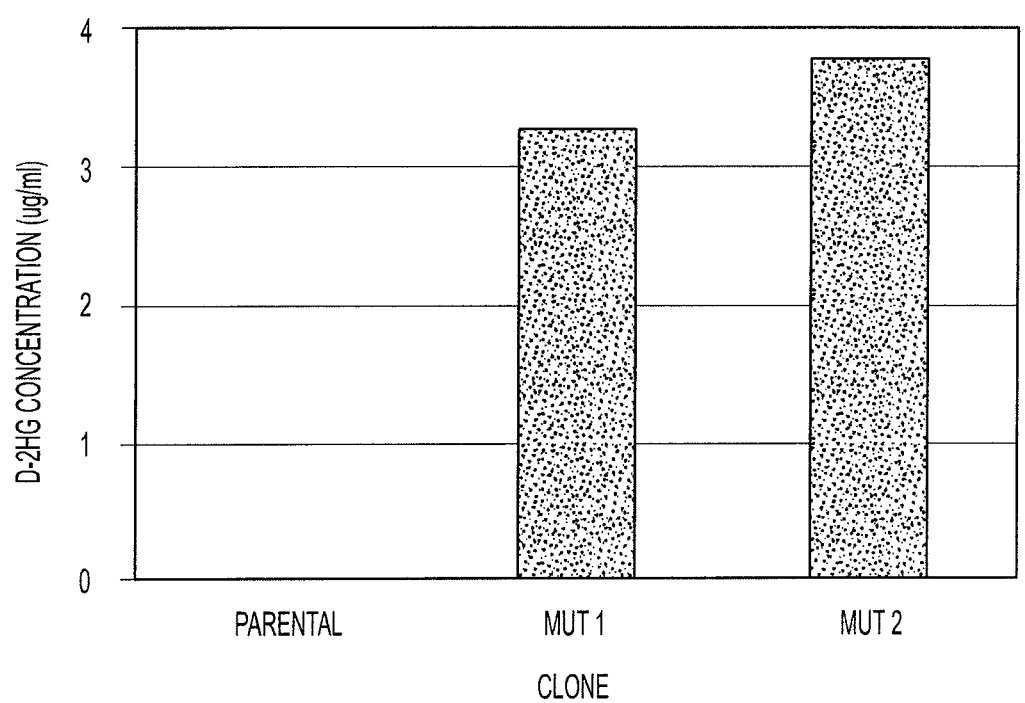
FIG. 6 is a graph showing two knock-in clones which express both the wild-type and mutant IDH1 cells produce high levels of D-2-HG. Parental cells are HCT116 parent clones, and MUT1 and MUT2 represent knock-in cells. $1 \times 10^6$ cells were plated in 6-well plates (3.5 ml/well) and media sample (McCoy's 5A) was taken after 48 hrs of culturing.
Figure 7:
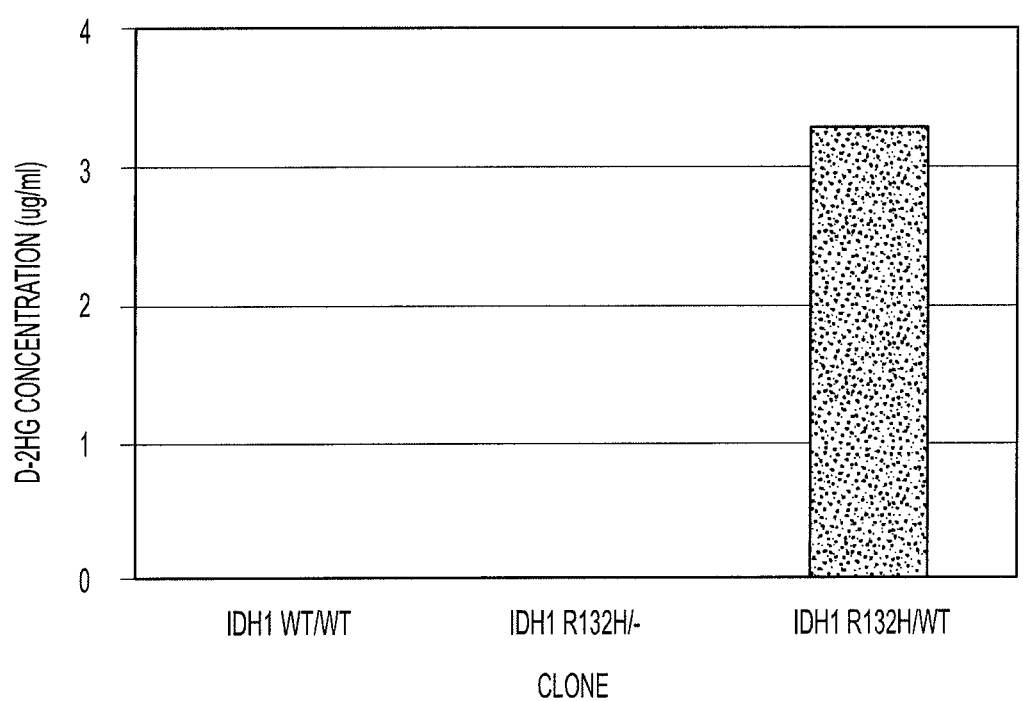
FIG. 7 is a graph showing D-2-HG production in IDH1 (IDH1R132H/−), IDH1 WT/WT and IDH1R132H/WT cells. $1 \times 10^6$ cells were plated in 6-well plates and media samples taken after 48 hours. One knock-in clone, IDH1R132H/−, which expresses only the mutant IDH1 gene, does not produce D-2-HG. However, the knock-in clone which expresses both the wild-type and mutant IDH1 gene (IDH1R132H/WT) produces high levels of D-2-HG.

As compared with other methods to inactivate or activate genes in cultured cells such as RNAi and recombinant protein expression systems, knock-in methods arguably provide the most powerful technique available to recapitulate naturally occurring genetic alterations. To achieve IDH1R132H mutations, established protocols were utilized for gene targeting via homolgous recombination with recombinant adeno-associated virus (rAAV) constructs. HCT116, a near diploid, mismatch repair-deficient cell line derived from colon carcinoma, is the most efficient and widely used human cell line for gene targeting. For IDH1 gene targeting, we used a HCT116-derived parental cell line. Targeting vectors were constructed to introduce $IDH1^{R132H}$ alleles in the HCT116 cell line (FIG. 1). An infectious rAAV stock harboring the targeting sequence was generated and applied to the parental cell line, generating cell clones that harbor the rAAV transgenes. A PCR-based method was employed to screen for correct homologous recombinants (FIG. 2). Next, excision of the selectable element was performed using a Cre adenovirus. Clones which achieved complete excision of the selectable element were identified using PCR-based and phenotypic (G418 sensitvity) assays (FIG. 3). Positively identified clones were subjected to sequencing analysis to validate knock-in of the mutation by genomic DNA and cDNA sequencing (FIG. 4 and FIG. 5). However, one clone with R132H knock-in in one allele of genomic DNA only expressed the mutant allele, with the WT IDH1 allele silenced (IDH1R132H/−) (FIG. 5). The precise mechanism of such silencing has not been determined. The knock-in clones were analyzed for D-2-HG production (FIG. 6 and FIG. 7). The clones that expressed both the wild-type and mutant alleles produced high levels of D-2-HG (FIG. 6), while the clone expressing only the mutant IDH1R132H produced low levels of D-2-HG (FIG. 7).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

We claim:

1. Isolated and purified human HCT116 colorectal cancer cells which comprise an IDH1 R132H allele and a wild-type IDH1 allele.

2. The cells of claim 1 wherein the cells produce more 2-hydroxyglutarate than isogenic wild-type IDH1 cells.

3. A kit comprising, in a divided container or multiple containers, a cell of claim 1 and at least one isogenic cell with a different IDH1 genotype.

4. The kit of claim 3 wherein the isogenic cell with a different IDH1 genotype is homozygous for wild type IDH1.

5. Isolated and purified human HCT116 colorectal cancer cells which comprise and express an IDH1 R132H allele, wherein the cells express no wild-type IDH1 mss.

6. The cells of claim 5 wherein the cells comprise one IDH1 R132 H allele.

7. The cells of claim 5 wherein the cells comprise an IDH1 allele which is transcriptionally silenced.

8. A pair of isogenic human HCT116 colorectal cancer cell lines, each member of said pair having a genotype selected from the group consisting of:
   a. IDH1 R132H/IDH1 wild-type;
   b. IDH1 wild type/IDH1 wild type; and
   c. IDH1 R132H/IDH1 wild-type transcriptionally silenced.

9. A kit comprising, in a divided container or multiple containers, the pair of cell lines of claim 8.

* * * * *